US007503923B2

(12) United States Patent
Miller

(10) Patent No.: US 7,503,923 B2
(45) Date of Patent: Mar. 17, 2009

(54) IMPACT HEAD ASSEMBLY FOR PERCUSSIVE THERAPEUTIC DEVICE

(76) Inventor: Edward W. Miller, P.O. Box 535, Salem, OR (US) 97308

(*) Notice: Subject to any disclaimer, the term of this patent is extended or adjusted under 35 U.S.C. 154(b) by 494 days.

(21) Appl. No.: 10/719,445

(22) Filed: Nov. 21, 2003

(65) Prior Publication Data

US 2005/0113870 A1 May 26, 2005

(51) Int. Cl.
*A61F 5/00* (2006.01)
*A61H 23/00* (2006.01)
*B25D 11/00* (2006.01)

(52) U.S. Cl. ......................... 606/238; 173/90; 173/114; 601/107; 601/111; 606/239

(58) Field of Classification Search ................. 601/107, 601/108, 109, 110, 111, 101, 103, 46, 97, 601/72, 73, 135, 137, 138, 78, 80; 606/237–239; 294/59; 403/297, 277, 280, 281; 81/463; 16/422; 173/90, 114, 117
See application file for complete search history.

(56) References Cited

U.S. PATENT DOCUMENTS

| | | | | | |
|---|---|---|---|---|---|
| 1,796,444 | A | | 3/1931 | Dell'era et al. | |
| 2,017,400 | A | * | 10/1935 | Hoyer | 601/135 |
| 2,048,220 | A | * | 7/1936 | Redding | 606/238 |
| 2,076,410 | A | | 4/1937 | McGerry | |
| 2,078,025 | A | | 4/1937 | Samuels | |
| 3,900,183 | A | * | 8/1975 | Wallace | 249/68 |
| 4,088,128 | A | | 5/1978 | Mabuchi | |
| 4,479,495 | A | * | 10/1984 | Isaacson | 606/204 |
| 4,549,535 | A | | 10/1985 | Wing | |
| 4,716,890 | A | | 1/1988 | Bichel | |
| 4,841,955 | A | | 6/1989 | Evans et al. | |
| 5,140,979 | A | | 8/1992 | Nakasawa | |
| 5,305,738 | A | * | 4/1994 | Shimizu | 601/75 |
| 5,519,923 | A | * | 5/1996 | Rojdev et al. | 27/1 |
| 5,618,315 | A | | 4/1997 | Elliott | |
| 5,673,455 | A | * | 10/1997 | Per-Lee et al. | 15/210.1 |
| 5,817,037 | A | * | 10/1998 | Zurbay | 601/135 |
| 5,843,005 | A | * | 12/1998 | Chubinsky | 601/15 |
| 6,228,042 | B1 | * | 5/2001 | Dungan | 601/107 |

(Continued)

FOREIGN PATENT DOCUMENTS

JP 57174533 A * 10/1982

OTHER PUBLICATIONS

English language translation of JP 57-174533 (PTO 09-0223) Oct. 2008.*

*Primary Examiner*—Stephen F Gerrity
(74) *Attorney, Agent, or Firm*—Carl D. Crowell

(57) ABSTRACT

An impact head for a chiropractic adjustment tool or tapper that is easy to install, remains stable during lateral movements and easily exchangeable. The impact head comprises a central bore having a bore diameter disposed in the impact head at the attachment end, an annular slot concentrically disposed and parallel to the impact head central bore extending into the impact head from the attachment end of the impact head. The impact head is then attached to a reciprocating rod having a rod center bore and an annular reciprocating rod insert end wherein the reciprocating rod attaches by inserting the reciprocating rod insert end into the annular slot of the impact head and in a central insert having an insert diameter inserted into the impact head central.

9 Claims, 2 Drawing Sheets

U.S. PATENT DOCUMENTS

| | | | | |
|---|---|---|---|---|
| 6,244,356 | B1 * | 6/2001 | Luna | 172/381 |
| 6,368,293 | B1 * | 4/2002 | Orgeron et al. | 601/15 |
| 6,537,236 | B2 * | 3/2003 | Tucek et al. | 601/80 |
| 6,602,211 | B2 * | 8/2003 | Tucek | 601/97 |
| 6,830,552 | B1 * | 12/2004 | Gonzalez | 601/137 |
| 6,964,214 | B2 * | 11/2005 | Wu | 74/551.8 |
| 7,122,015 | B2 * | 10/2006 | Luettgen et al. | 601/73 |
| 7,144,417 | B2 * | 12/2006 | Colloca et al. | 606/239 |
| 7,169,169 | B2 * | 1/2007 | Tucek et al. | 606/239 |
| 2001/0010105 | A1 * | 8/2001 | Flanz | 15/145 |
| 2002/0082532 | A1 * | 6/2002 | Tucek et al. | 601/97 |
| 2002/0169400 | A1 * | 11/2002 | Huang | 601/111 |
| 2003/0009118 | A1 * | 1/2003 | Sabo et al. | 601/137 |
| 2005/0187498 | A1 * | 8/2005 | Miller | 601/72 |
| 2006/0041208 | A1 * | 2/2006 | Ko | 601/15 |
| 2006/0155224 | A1 * | 7/2006 | Calvert | 601/111 |
| 2006/0173389 | A1 * | 8/2006 | Chai | 601/135 |

* cited by examiner

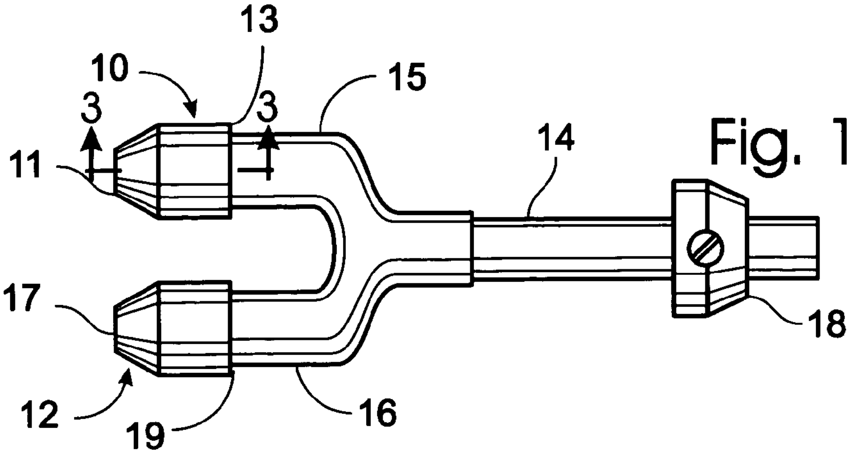
Fig. 1
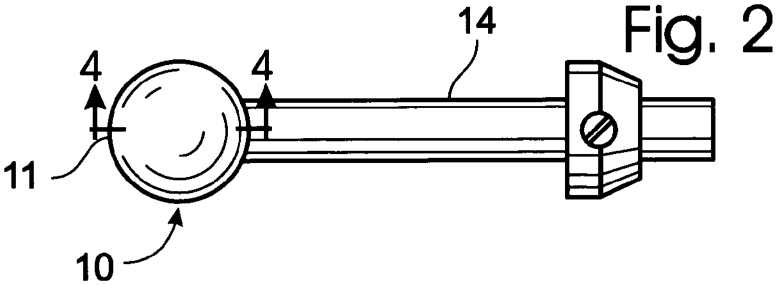
Fig. 2
Fig. 3
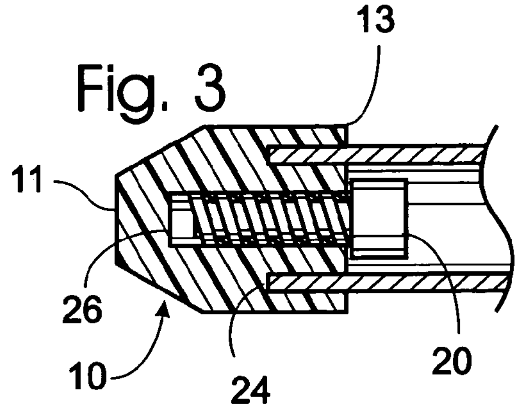
Fig. 4
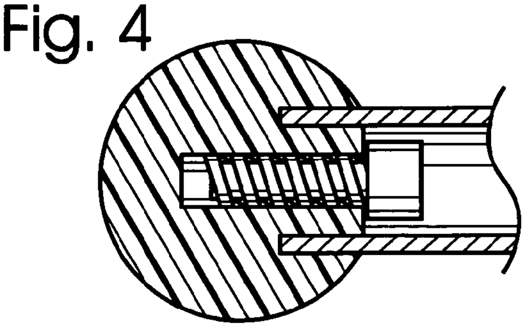

Fig. 5
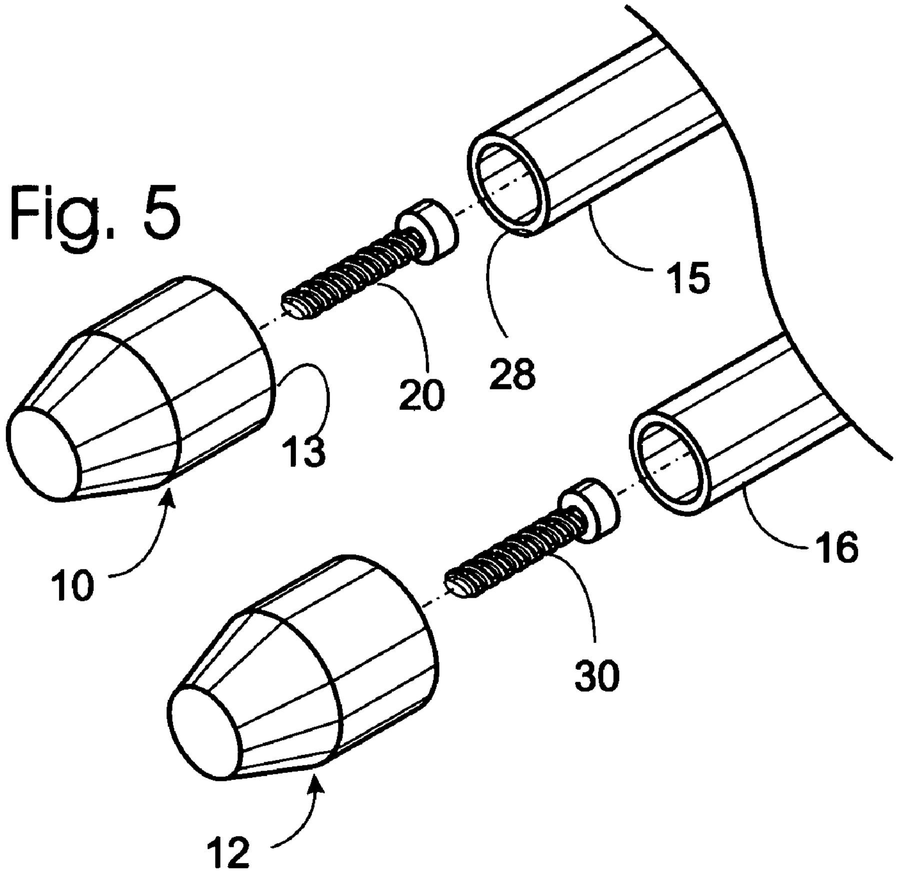
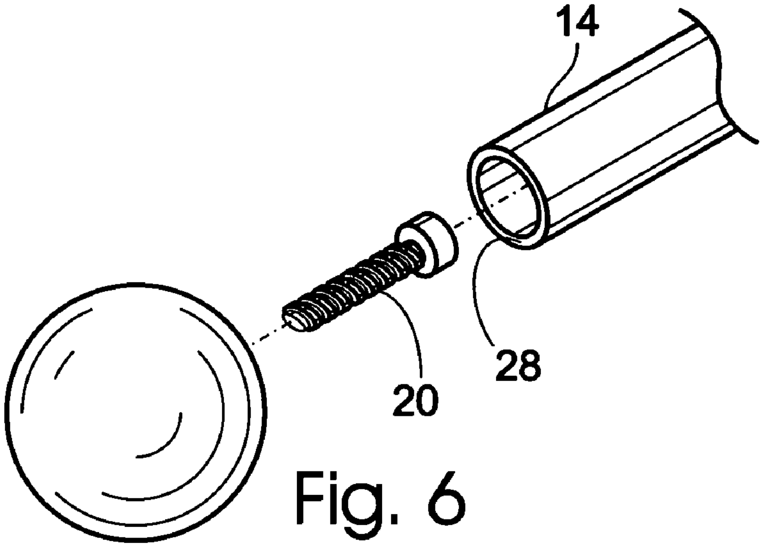
Fig. 6

IMPACT HEAD ASSEMBLY FOR PERCUSSIVE THERAPEUTIC DEVICE

BACKGROUND OF THE INVENTION

The present invention involves the field of medical devices. More particularly, it involves the field of percussive medical devices used as chiropractic adjustment tools used to move bones and relieve muscle spasms and stress. Even more particularly, it relates to an improved head assembly for a percussive therapeutic device.

Percussion is a relatively new treatment modality for those who suffer from musculoskeletal pain and myofascial trigger syndrome. It is a non-surgical, non-invasive procedure that may serve as a therapeutic alternative to trigger point and epidural injections. Percussion may also be used when other treatments have failed. Performed on an outpatient basis, percussive treatment carries little or no risk and is relatively comfortable.

As is well-known in the chiropractic art, the spines or other bones of humans sometimes go out of alignment or are otherwise mis-adjusted. This can lead to discomfort and additional physical symptoms. In such cases an adjustment of the spine or other bone to a healthy alignment can have substantial therapeutic effects.

Several attempts have been made to provide hand-held manual, pneumatic, or electric vibratory devices to assist in adjusting a patient's spine or other bones by the use of successive impacts. Typically these devices have a soft or pliable head or tip that makes direct contact with the patient's body. For the patient's comfort, these heads are made from a much softer material than the driving mechanism behind them. As a result, the heads have a tendency to creep or become disconnected from the driving mechanism when lateral force is applied. This may cause pain to the patient as well as frustration to the physician due to continuous replacement of heads during a treatment.

Needed in the field is a percussive device that allows the physician to apply adequate lateral pressure to the head of the device without causing the head to disconnect from the assembly. Additionally, there is a need for the impact head to be quickly and easily exchanged for another shape or size if needed during a therapy session. The present invention is directed to these shortcomings in the prior art.

BRIEF SUMMARY OF THE INVENTION

The present invention provides a chiropractic adjustment tool or tapper, which, generally, comprises a housing, with or without a handle and a motor or power source to drive an axially reciprocating rod. The reciprocating rod is disposed perpendicularly or near perpendicularly to the handle. One end of reciprocating rod extends from the housing which has a spring pair assembly to permit the ready adjustment of impact force and axial travel of the reciprocating rod. The opposite end of the reciprocating rod has an attached impact head.

The operation of the device is with a solenoid, or other motive force driving the reciprocating rod axially. The reciprocating rod is slidealbly mounted within the housing, transiting through the solenoid coil. The reciprocating rod is held in place by springs, affixed to the reciprocating rod to limit travel and to return the reciprocating rod to the neutral position between impacts. On activation, the reciprocating rod is accelerated axially by the solenoid or other motive force. Mounted on the extended end of the reciprocating rod is one of a variety of impact heads. An impact head is used to impact the patient's body. The shape of the impact head is determined by the treatment required. When the solenoid is reactivated, the reciprocating rod is again accelerated toward the Patient's body. A typical rate of impact is twelve impacts per second. Both the speed and the force of impact are adjustable to provide optimal therapeutic effects.

In the preferred embodiment the impact head, which can be made of a pliable materials such as plastic, rubber, or silicone rubber, is attached by a two stage process. First, the reciprocating rod, which is preferably tubular, is inserted into an annular slot in the impact head approximately equidistant from a center bore of the impact head and the outer most edge of the impact head. The outer shape of the impact head is not limited to any one embodiment. The contact end of the impact head which is what comes in contact with the patient can be round, flat, coned or any other shape applicable in the task. The reciprocating rod can be forked like that of FIG. 1 so more than one impact head may be attached at the same time. Although FIG. 1 shows only coned shaped impact heads, any shaped impact heads may be attached.

The hole or center bore of the impact head is preferred as it makes for easy installation upon twisting. The inner column created by the center bore and the annular slot experiences a reduced diameter upon twisting, and then returns to its original size when released from twisting thereby fitting tightly within the annular slot.

Secondly, in the preferred embodiment, a central insert, which may be made of plastic that is rigid to semi-rigid in nature is placed into the center bore of the impact head. The central insert is a rigid or semi-rigid material of a generally rod shape that permits some lateral movement of the impact head, but limits axial travel and prevents excessive creep or displacement of the impact head when in use. The central insert may be threaded or ribbed to further secure the central insert into the center bore. Further benefits of the invention include the central insert's limiting compression of the center bore, further securing the reciprocating rod to the annular slot.

Improvement over the prior art is found in the stability of the connection of the impact head to the reciprocating rod. The impact head grips both the inside and the outside of the reciprocating rod with the annular slot insertion. In the preferred embodiment, when the central insert is placed in the central bore, this provides added rigidity, serves as an anvil, and prevents excessive lateral displacement in side loading. The central insert is also in position to provide improved transmission of force by providing an rigid linear anvil element, reducing the force absorption of any elastic material used to form the impact head. The central insert also helps prevent the impact head from dislodging on side or lateral loading. The added lateral stability however, will not impact the ease of replacing the impact head when needed. The user can simply pull the impact head off the reciprocating rod and reinstall a different shaped impact head depending on what the treatment requires.

For a more complete understanding of the present invention, reference is made to the following detailed description and accompanying drawings. In the drawings, reference numbers refer to like parts through the several views.

BRIEF DESCRIPTION OF THE DRAWINGS

FIG. 1 is plan view of a forked reciprocating rod with impact head assembly of a percussive adjusting tool in accordance with a preferred embodiment of the present invention;

FIG. 2 is a plan view of a reciprocating rod with an alternate embodiment of the impact head;

FIG. 3 is a cross section view of the invention along the 3-3 line of FIG. 1.

FIG. 4 is cross section view of the invention along the 4-4 line of FIG. 2.

FIG. 5 is an exploded view of the impact head to reciprocating rod attachment depicted in FIG. 1.

FIG. 6 is an exploded view of the impact head to reciprocating rod attachment depicted in FIG. 2.

DETAILED DESCRIPTION OF THE DRAWINGS

Referring to the drawings, FIG. 1 is a plan view of a reciprocating rod and impact head assembly of a percussive chiropractic adjusting tool in accordance with the preferred embodiment of the invention. Reciprocating rod 14 is fixably attached at one end to a drive connector means 18. Attached to drive connector means 18 is a housing (not shown) with or without a handle and a motor or power source to drive the axially reciprocating rod 14. In this preferred embodiment, the opposing end of reciprocating rod 14 is split into a first reciprocating rod 15 and a second reciprocating rod 16.

A first reciprocating rod 15 is attached to an impact head 10 at an impact head attachment end 13 and a second reciprocating rod 16 is attached to a second impact head 12 at a second impact head attachment end 19. The contact end 11 is the opposite end of the impact head 10 from the impact head attachment end 13. The second impact head contact end 17 is the opposite end of the second impact head 12 from the second impact head attachment end 19. The contact end 11 and second contact end 17 typically contact the body at the same time providing a parallel treatment, for example, down either side of the spine.

FIG. 2 is a side elevation view of an alternate impact head embodiment attached to a straight or non-forked reciprocating rod.

FIG. 3 is a cross-section taken along line 3-3 in FIG. 1 illustrating the relationship of the impact head with respect to the central insert and the reciprocating rod of the preferred embodiment of the invention. The reciprocating rod insertion end 28 of the first reciprocating rod 15 is inserted into an annular slot 24 which is disposed axially into the attachment end 13 of the impact head 10. The central insert 20 is inserted into the impact head central bore 26 of the impact head 10, or may be threaded if the central insert 20 has threads. The central insert 20 can be made from a rigid or semi-rigid material. Additionally, the central insert 20 provides added rigidity, serves as an anvil and prevents excessive lateral displacement during side loading on impact head 10 as well as prevents the impact head 10 from dislodging upon side or lateral loading by preventing compression of the central bore 26.

FIG. 4 is a side elevation view in a cross-section taken along line 4-4 in FIG. 2 illustrating the relationship of the impact head with respect to the central insert and reciprocating rod of an alternate embodiment.

FIG. 5 is an exploded view of the impact head 10 to the first reciprocating rod 15 attachment and second impact head 12 to second reciprocating rod 16 attachment of the preferred embodiment of the present invention. The central insert 20 is inserted into the impact head central bore 26 at the attachment end 13 of the impact head 10. The reciprocating rod insertion end 28 of the first reciprocating rod 15 is inserted into the annular slot 24 preferably with a twisting motion.

FIG. 6 is an exploded view of the impact head 10 depicted in FIG. 4. The reciprocating rod insertion end 28 of the reciprocating rod 14 is inserted into the annular slot 24 with a twisting motion The central insert 20 is inserted into the impact head central bore 26 at the attachment end 13 of the impact head 10.

Wherein the terms and expressions which have been employed in the foregoing specification are used therein as terms of description and not of limitation, there is no intention, in the use of such terms and expression, of excluding equivalents of the features shown and described or portions thereof, it being recognized that the scope of the invention is defined and limited only by the claims which follow.

I claim:

1. An impact head assembly for a percussive therapeutic device, comprising:

an elastic impact head having a contact end opposite an attachment end;

an elastic impact head central bore having a bore diameter disposed in said elastic impact head at said attachment end and extending toward said contact end having an elastic impact head central bore base as a farthest extension of said elastic impact head central bore;

an annular slot concentrically disposed and parallel to said elastic impact head central bore extending into said elastic impact head from said attachment end of said elastic impact head;

a central insert having an insert diameter insertable into said elastic impact head central bore of said elastic impact head; and a reciprocating rod insertable into said annular slot concentrically disposed and parallel to said elastic impact head central bore, whereby the elastic nature of the said elastic impact head adheres to the said reciprocating rod as it reciprocates.

2. An Impact head assembly for a percussive therapeutic device of claim 1 wherein said contact end of said elastic impact head is flat.

3. An impact head assembly for a percussive therapeutic device of claim 1 wherein said contact end of said elastic impact head is round.

4. An impact head assembly for a percussive therapeutic device of claim 1 wherein said contact end of said elastic impact head is cone-shaped.

5. An impact head assembly for a percussive therapeutic device of claim 1 wherein said elastic impact head is made of silicone rubber.

6. An impact head assembly for a percussive therapeutic device of claim 1 wherein said elastic impact head is made of plastic.

7. An impact head assembly for a percussive therapeutic device of claim 1 wherein said central insert is threaded or ribbed.

8. An impact head assembly for a percussive therapeutic device of claim 1 wherein said central insert is made of rigid plastic.

9. An impact head assembly for a percussive therapeutic device of claim 1 wherein said central insert is made of semi-rigid plastic.

* * * * *